(12) United States Patent
Johnson

(10) Patent No.: US 11,302,454 B2
(45) Date of Patent: Apr. 12, 2022

(54) PERSONAL RADIATION PROTECTION GARMENT USING RADIATION PROTECTIVE LAYERS

(71) Applicant: Burlington Medical, LLC., Newport News, VA (US)

(72) Inventor: Denise Johnson, London (GB)

(*) Notice: Subject to any disclaimer, the term of this patent is extended or adjusted under 35 U.S.C. 154(b) by 0 days.

(21) Appl. No.: 16/586,971

(22) Filed: Sep. 28, 2019

(65) Prior Publication Data
US 2021/0082592 A1    Mar. 18, 2021

(30) Foreign Application Priority Data
Sep. 16, 2019 (GB) .................................. 1913335

(51) Int. Cl.
*A61B 6/10* (2006.01)
*G21F 3/02* (2006.01)

(52) U.S. Cl.
CPC ............... *G21F 3/02* (2013.01); *A61B 6/107* (2013.01)

(58) Field of Classification Search
None
See application file for complete search history.

(56) References Cited

U.S. PATENT DOCUMENTS

2010/0163758 A1\* 7/2010 Kirschenbaum ............................
                                                    A61F 13/49007
                                                    250/516.1
2014/0150154 A1\* 6/2014 Aquino ..................... F41H 1/02
                                                    2/2.5
2018/0000432 A1\* 1/2018 Pruyne ................... A61B 6/032

FOREIGN PATENT DOCUMENTS

JP          2019094602 A   \*   6/2019

OTHER PUBLICATIONS https://web.archive.org/web/20140717100320/http://workroomsocial.com/blog/how-to-make-single-welt-pockets/ (Year: 2014).\*

\* cited by examiner

*Primary Examiner* — James Choi
(74) *Attorney, Agent, or Firm* — Michael L. Greenberg, Esq.; Greenberg & Lieberman, LLC

(57) ABSTRACT

A personal radiation protection garment apparatus is described. The garment is equipped with multiple layers, including a central protective layer, which helps to prevent the unwanted application of radiation to an individual when worn. Multiple sections of the garment are joined by overlapping seams. The protective layer includes a first and a second partially lapping radiation-protective panels, with the first panel attached to the first layer at a first attachment zone, and the second panel attached to the second layer at a second attachment zone. The first panel is configured to overlap the second panel across the second attachment zone, providing a continuous protective covering of the second attachment zone, and the second panel overlaps the first panel across the first attachment zone as well.

14 Claims, 3 Drawing Sheets

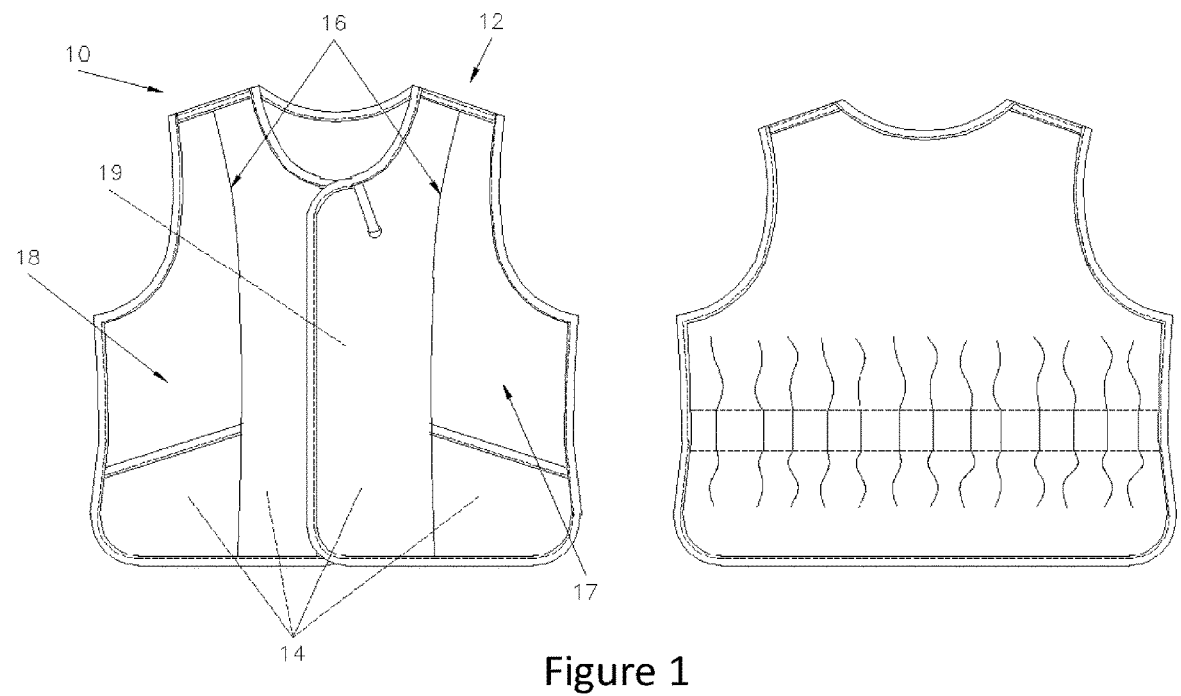
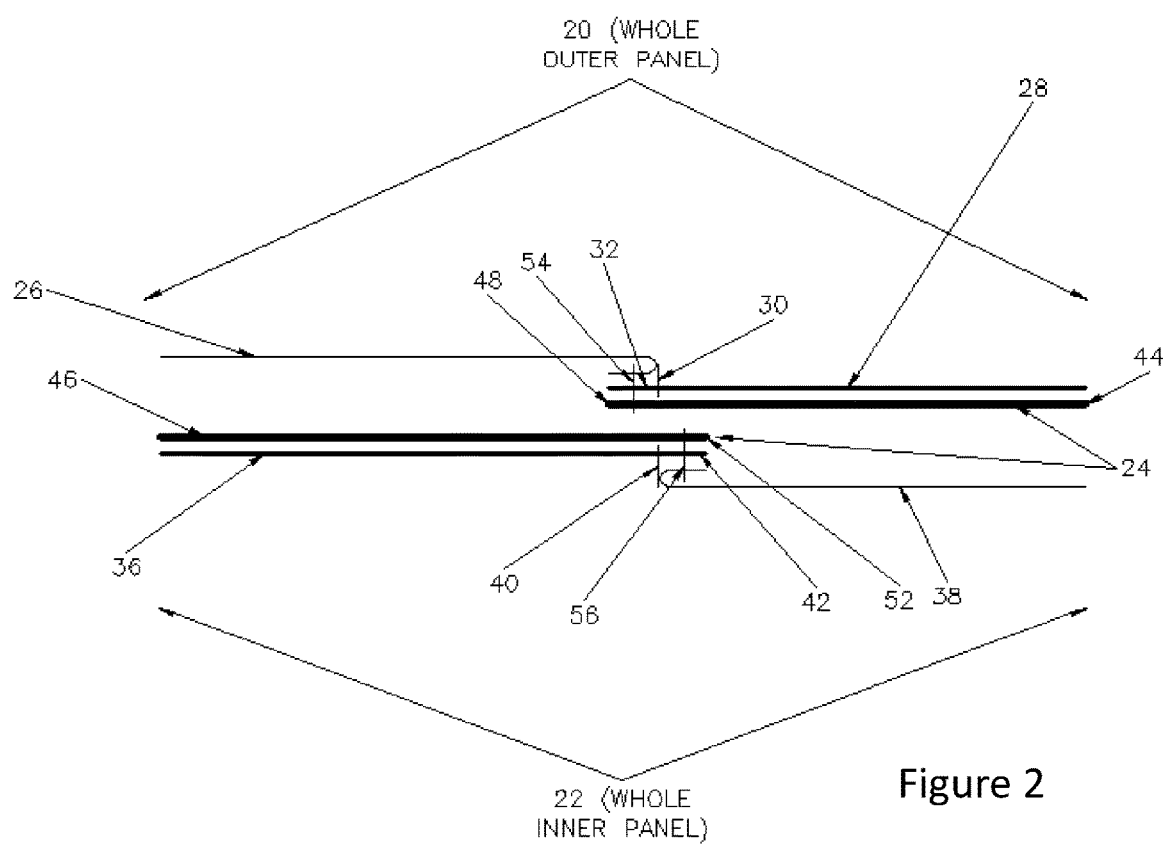
Figure 1
Figure 2

PERSONAL RADIATION PROTECTION GARMENT USING RADIATION PROTECTIVE LAYERS

CONTINUITY

This application is a non-provisional patent application of UK patent application number 1913335.4, filed on Sep. 16, 2019, and priority is claimed thereto.

FIELD OF THE PRESENT INVENTION

The present invention relates to the field of protective garments, and more specifically relates to a personal radiation protection garment for use in the presence of radiation.

BACKGROUND OF THE PRESENT INVENTION

There are various situations in which people work in the presence of radiation. One example of such a situation is in a medical context in which a clinical practitioner works in the presence of x-rays or other radiation as that radiation is being used on a patient for a clinical purpose or is present as a result of a clinical procedure. If the clinical practitioner is unprotected, such radiation can potentially be harmful, especially if the clinical practitioner is exposed many times in many such procedures.

As a result, such clinical practitioners generally wear a personal radiation protection garment. Conventional methods of producing such a garment often involve using a flat 2D panel of protective core material (a Lead resin mix). Reference is made to IEC Standard IEC61331-3, 2014 Edition 2, Part 3 Protective clothing, Section 5.

Using such conventional garments, the core protective material cannot be formed to become a convex 3D shape over the breast of a female wearer without applying seams to the core material. However, this is not generally desired as it will generally result in perforation occurring which in turn will allow harmful radiation to pass through to the breast tissue of the wearer. Due to this restriction, the results are a flat garment which is more cumbersome, ill-fitting around the breast area and heavier for the wearer, resulting in poorer performance. The wearer either must accept a flat garment without shape, which is either very tight and thus crushes the breast tissue to hold it flat to the body, or very loose, which allows harmful radiation to penetrate the side of the breast.

Some types of radiation protection clothing are disclosed in JP3206558U, JP3210260U, and DE202017106976U1.

In general, substantially continuous protective panels are particularly effective at shielding a user from radiation and are often desired in a clinical setting. Aspects of the present invention seek to provide an improved personal radiation protection garment.

SUMMARY OF THE PRESENT INVENTION

The present invention is a personal radiation protection garment configured for use on an individual. According to an aspect of the invention, there is provided a personal radiation protection garment, including:
a first layer;
a second layer;
a protective layer between the first and second layers;

wherein the first layer includes first and second sections joined at a first seam, and the second layer includes third and fourth sections joined at a second seam;

wherein the protective layer includes first and second partially lapping radiation-protective panels, the first panel being attached to the first layer at a first attachment zone and the second panel being attached to the second layer at a second attachment zone;

wherein the first panel laps the second panel across the second attachment zone to provide a continuous protective covering of the second attachment zone, and the second panel laps the first panel across the first attachment zone to provide a continuous protective covering of the first attachment zone.

Some optional features are discussed in the dependent claims below. Embodiments are able to provide a garment which follows the contours of the female form.

Embodiments are able to provide a solution to the problems of ill-fitting garments by providing for the construction and shape of a convex seam to shape over the breast tissue, giving the advantage of fit and protection.

In some embodiments, the design of the construction allows the flat, protective core material, to be fitted much closer over the shape of the breast, lymph nodes, axilla, and front neck areas whilst giving greater comfort and protection, without impediment of movement for the wearer.

Embodiments can be used to provide the wearer with protection from sources of harmful scatter radiation in a clinical environment, paying attention to the delicate breast area, lymph nodes and the axilla. Unlike many conventional garments which cannot be molded over the female form around the breast area, garments according to embodiments of the invention can be provided with seams which allow the garment to be shaped to fit the body, especially the female form, much better.

In some embodiments, the construction of a seam involves the sewing of 2 cm, flat open seams, on both inner and outer materials, then lapping the seam extension on the core material over the seam on the outer fabric. In such embodiments, the same application can then be applied to the inner lining seam. The lead core material can then be tacked into position along the outer edge of the seam allowance. The seams can then be mounted on top of each other with the core material and seam allowances lying in opposite directions. The opposing seams can then be lapped to create a double layer of internal core material in this area which will shield the front body portion of the wearer from any radiation which may pass through the puncture holes created whilst tacking the core material into position. The core material can be attached to opposing seams and finished with a bound edge so it cannot be stretched further than the controlling panel of fabric.

The following brief and detailed descriptions of the drawings are provided to explain possible embodiments of the present invention but are not provided to limit the scope of the present invention as expressed herein this summary section.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

The present invention will be better understood with reference to the appended drawing sheets, wherein:

FIG. 1 is a front and back view of a garment according to an embodiment of the invention;

FIG. 2 is a view of the interior of the thickness of a garment according to an embodiment of the invention;

DETAILED DESCRIPTION OF THE PREFERRED EMBODIMENT

Figure 3:
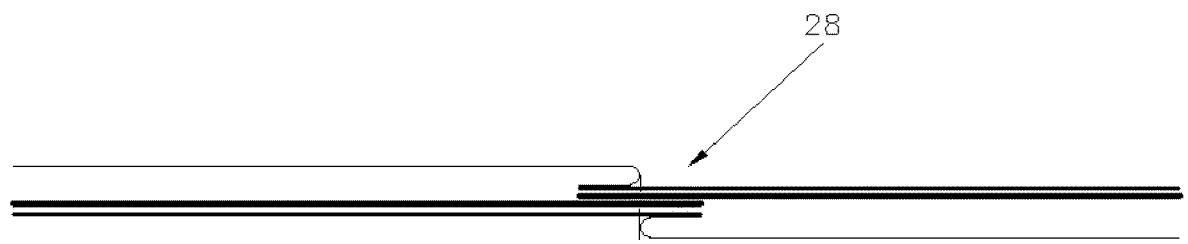
FIG. 3 is another view of the thickness of the garment of the embodiment of FIG. 2.

The present specification discloses one or more embodiments that incorporate the features of the invention. The disclosed embodiment(s) merely exemplify the invention. The scope of the invention is not limited to the disclosed embodiment(s).

References in the specification to "one embodiment," "an embodiment," "an example embodiment," etc., indicate that the embodiment described may include a particular feature, structure, or characteristic, but every embodiment may not necessarily include the particular feature, structure or characteristic. Moreover, such phrases are not necessarily referring to the same embodiment, Further, when a particular feature, structure, or characteristic is described in connection with an embodiment, it is submitted that it is within the knowledge of one skilled in the art to effect such feature, structure, or characteristic in connection with other embodiments whether or not explicitly described.

Embodiments of the invention are directed at an improved personal radiation protection garment with a specially constructed seam which allows for the garment to be shaped over curved areas of the wearer's body. Preferred embodiments are particularly directed to an improved apron construction which involves applying a specially constructed seam over the breast area of the garment and down the front of the body.

The specially constructed seam allows shape to be introduced to the core protective material which conventionally has generally been constructed and manufactured as a flat panel joined at the sides of the body. The seam is designed in such a fashion to continue to protect the wearer whilst improving fit, comfort, weight and protection.

Since the likelihood of radiation leaks is increased due to punctures of the core material, the specially constructed seam has been developed in such a way as to avoid any exposed punctures in the area of the seam, while allowing for example a convex shape to be introduced to the garment by using several different panels, for example by cutting the fronts into separate panels.

By providing separate panels and constructing them as described below, the improvement of fit and greater protection is enhanced and there are advantages to be gained when compared with conventional construction using a flat sheet of core lead material. The garment can be fitted far better enabling a closer fit to the axilla and following of the shape of the body in this area, giving huge benefits particularly to female wearers of personal radiation protection garments.

FIG. 1 shows the front and back of a personal radiation protection garment 10 according to an embodiment of the invention, in particular an apron designed to cover the front of a wearer's body. Within the thickness of the garment at the front 12 of the garment, the garment includes a first layer and a second layer, which in this embodiment form the inner and outer layers of the garment. The garment also includes a protective layer between the first and second layers. The protective layer is the operative layer of the garment which serves to shield the wearer from scatter radiation.

The protective layer includes a plurality of panels 14 which cannot be seen in FIG. 1 but which meet in the region of seam arrangements 16. Each of the panels is a substantially two-dimensional sheet of radiation protective material. In this embodiment, the radiation protective material is a lead material, in particular a lead resin mix; however, in other embodiments the protective material can be a lead-free protective material. Also, the skilled person will be aware of other radiation protective materials that can be used in other embodiments.

Rather than having a single panel which has the disadvantage of being difficult to shape as described above, the use of a plurality of panels can allow seam arrangements 16 at the regions where two panels meet and a desired convex 3D shape to be achieved. In the embodiment shown in FIG. 1, the garment is a jacket-type with a left front side 17 and a right front side 18 which can be releasably fastened together by a zip 19, although other fastening mechanisms can be used in other embodiments. In this embodiment, there are four panels 14 which are shaped and arranged in the manner shown, two on the right front side 18 and two on the left front side 17. The seam arrangements 16 extend from the shoulder to the hem in a curved configuration to form a convex 3D shape particularly suitable for female wearers. Nevertheless, the skilled person will be able to arrange the panels in a different configuration and/or use a different number of panels in order to achieve a different shape as desired.

As has been described above, a potential risk with using multiple panels and seams to provide a better fit is that the seams are likely to result in perforation in the protective layer which can allow harmful radiation to pass through. Embodiments of the present invention are able to obviate this risk as explained below with reference to FIG. 2.

FIG. 2 shows the interior of the garment as a cross-section through the thickness in the region of a seam arrangement 16 of the garment of FIG. 1. The description relating to FIG. 2 relates to the seam arrangement 16 where two of the shaped panels 14 meet, and this description is applicable to any of the regions where two panels meet in the garment, particularly to panels that meet at the front 12 of the garment.

The description uses the term "longitudinal" to refer to the direction of the seams. The skilled person will understand that the term "longitudinal" as used herein refers to a longitudinal direction of the seams at a particular region where two panels meet and does not refer to a global longitudinal direction with respect to the garment as a whole since the seams of the garment may extend in different directions in different parts of the garment. Furthermore, the longitudinal direction is the direction of the seams in question and it is not necessarily the case that this is a straight line.

FIG. 2 shows the first layer 20, the second layer 22 and the protective layer 24 between the first and second layers. The first layer 20 includes a first section 26 and a second section 28. The first and second sections 26, 28 are in this embodiment sections of fabric and are substantially two-dimensional sheets thereof. However, in other embodiments they can be made of any other appropriate material for inner and outer layers of a radiation protective garment.

The first and second sections 26, 28 are joined at a first seam 30 which runs in the longitudinal direction. The first seam is the part of the seam arrangement 16 that can be seen from the front of the garment.

Figure 5:
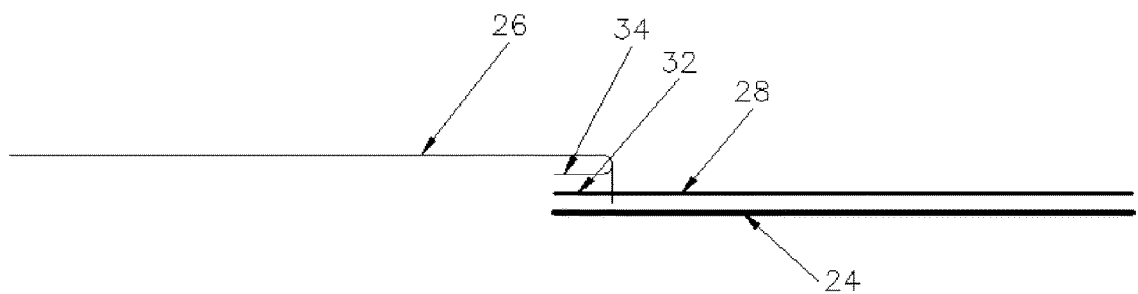
FIG. 5 is a view of the interior of the thickness of the garment of the embodiment of FIGS. 2 to 4.

The first layer 20 includes a first flap 32 which extends radially internally with respect to the garment, away from the first seam 30 and towards the second layer 22. As can be seen, the first flap 32 extends from the first seam 30. The first flap 32 can be an extension of either the first or the second section 26, 28, in other words it can be a seam allowance, or in other embodiments it can be an entirely separate piece of material which is attached to the first seam 30. In this embodiment, the first flap 32 is an extension of the second section 28 extending over the first section as shown in FIG. 5. However, in another embodiment, the first flap 32' can be an extension of the first section 26 folded open over the first section as can be seen in FIG. 6.

Figure 6:
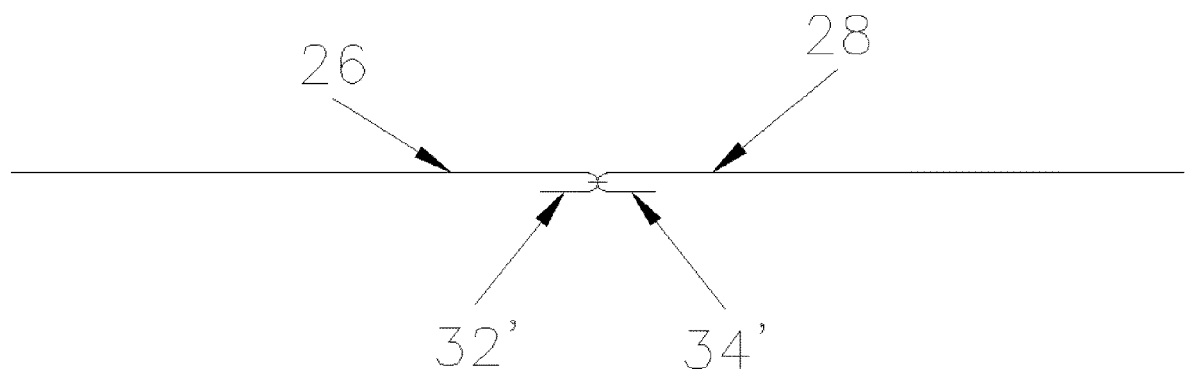
FIG. 6 is a view of the interior of the thickness of a garment according to another embodiment of the invention.

As can be seen in FIGS. 5 and 6, the section which does not extend into the first flap 32 can extend and form a further flap 34, 34'. However, this is not necessary in every embodiment.

In this embodiment, the first section and its extension are formed from a single piece of material and the second section and its extension are formed from a single piece of material. However, in other embodiments, separate pieces of material can be joined to form the sections and extensions.

The flaps can be considered to extend from a near end at the first seam 30 to a remote end away from the first seam 30. In this embodiment the remote end includes the edge of the piece of material that forms the second section and its extension.

As can be seen in FIG. 2, the second layer 22 includes a third section 36 and a fourth section 38. Like the first and second sections 26, 28, these are in this embodiment sections of fabric, and are substantially two-dimensional sheets thereof. However, as for the first and second sections, the skilled person will be aware that other materials can be used in other embodiments.

The third and fourth sections are joined at a second seam 40. In this embodiment, the first and second seams 30, 40 are aligned such that there is substantially no lateral distance between them, wherein the term "lateral" is intended to refer to a direction transverse to the longitudinal direction. Nevertheless, in other embodiments, the first and second seams 30, 40 can be laterally spaced provided that the attachment zones of the protective layer are still covered as described below.

The third section is substantially opposite the first section and the fourth section is substantially opposite the second section. In other words, the first section is generally on a first lateral side of the first seam and the third section is generally on the first lateral side of the second seam, whereas the second section is generally on a second lateral side of the first seam and the fourth section is generally on the second lateral side of the second seam, wherein the second lateral side is opposite to the first lateral side. The first and third sections are generally on the same lateral side of the first and second seams and the second and fourth section are generally on the same lateral side of the first and second seams.

The second layer 22 includes a second flap 42 which extends from the second seam 40, away from the second seam 40, radially internally with respect to the garment, towards the first layer 20.

As for the first flap 32, the second flap 42 can be an extension of the third or fourth sections 36, 38, in other words it can be a seam allowance, or can be an entirely separate piece of material which is attached to the second seam 40. In this embodiment, the second flap 42 is an extension of the third section 36 and is configured in a corresponding way to the first flap shown in FIG. 5. However, in another embodiment, the second flap can be configured in a corresponding manner to that shown for the first flap in FIG. 6.

The section which does not extend into the second flap 42 can extend to form a further flap in a corresponding manner to the further flap 34, 34' shown in FIGS. 5 and 6. However, this is not necessary in every embodiment.

In the embodiment of FIG. 2, the third section and its extension are formed from a single piece of material and the fourth section and its extension are formed from a single piece of material. However, in other embodiments, separate pieces of material can be joined to form the sections and extensions.

The second flap can be considered to extend from a near end at the second seam 40 to a remote end away from the second seam 40. In this embodiment the remote end includes the edge of the piece of material that forms the third section and its extension.

In this embodiment, the first and second flaps 32, 42 extend laterally away from each other and from both the first and second seams 30, 40. This is preferably also the case in other embodiments, even if the seams are not aligned, in order to increase overlap of the panels.

The first and second seams are in this embodiment 2 cm flat open seams, although other types of seams can be used in other embodiments.

Figure 4:
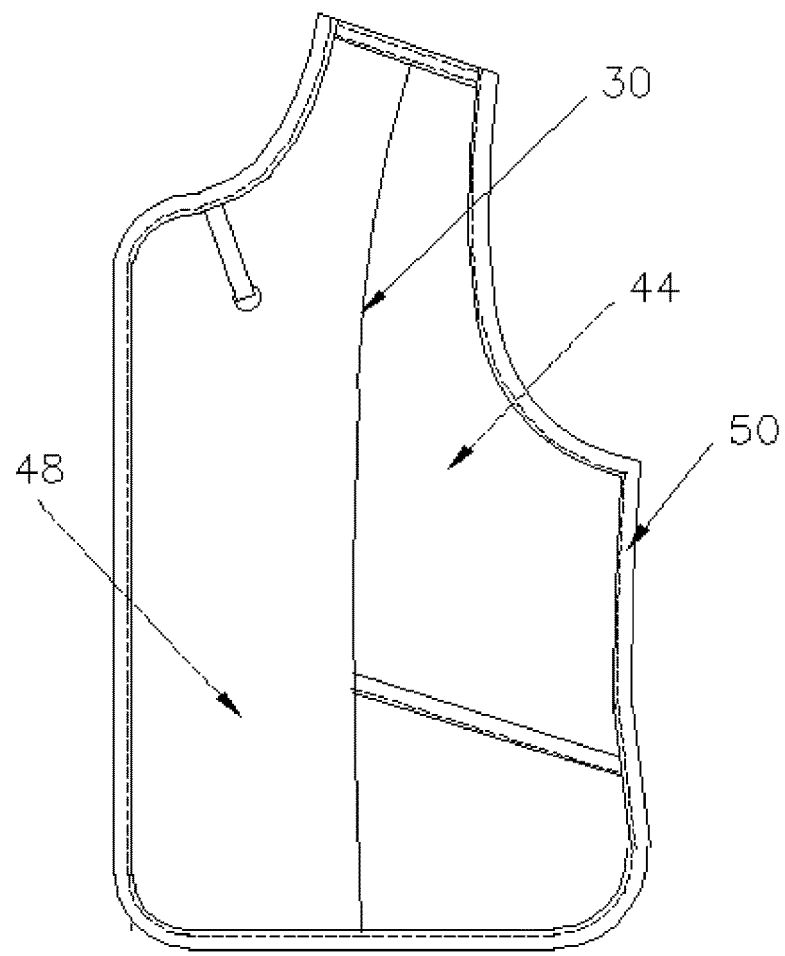
FIG. 4 is a front view of the garment of the embodiment of FIGS. 2 and 3.

The protective layer includes first 44 and second 46 partially lapping radiation protective panels, which are in this embodiment two of the panels 14 described in connection with FIG. 1 as explained above. In this embodiment, the first panel 44 includes a lapped edge 48 and a bound edge, the bound edge not being visible in FIG. 2. At the bound edge, the first panel 44 does not lap another panel but is secured by being bound to the first and second layers 20, 22. This is not necessary in every embodiment, but it can help to prevent the panels from being pulled apart in the vicinity of the first and second seams 30, 40 such that they no longer overlap. The bound edge may be an edge opposite and/or adjacent to the lapped edge. Reference is made to FIG. 4 which shows an example of the location of a bound edge 50 at an opposite edge of the first panel 44 to the lapped edge 48.

In a similar manner, the second panel 46 includes a lapped edge 52 and a bound edge. In the depicted embodiment, the first panel has a bound edge at its entire periphery where it does not meet the second panel and the second panel has a bound edge at its entire periphery where it does not meet the first panel. The first panel 44 laps the lapped edge 52 of the second panel 46 and the second panel 46 laps the lapped edge 48 of the first panel 44.

The first panel laps no more than 50% of the area of the second panel and the second panel laps no more than 50% of the area of the first panel. In particular, the first panel laps no more than 25% of the area of the second panel and the second panel laps no more than 25% of the area of the first panel.

The lapped edge 48 of the first panel 44, and the lapped edge 52 of the second panel 46, extend substantially in the longitudinal direction and are laterally spaced from each other and from the first and second seams 30, 40.

As can be seen from FIG. 2, the lapped edges of the first and second panels are on opposite sides of the first and second seams 30, 40 so that, radially between the first and second seams 30, 40, the first and second panels 44, 46 overlap. In embodiments in which the seams are not aligned, the first and second panels lap at least in the region laterally between the first and second seams.

The first panel 44 is attached to the first layer, in particular to the first flap 32, at a first attachment zone 54 which extends in the longitudinal direction along the lapped edge 48 of the first panel 44 and along the remote end of the first flap 32.

Similarly, the second panel 46 is attached to the second layer 22, in particular to the second flap 42, at a second attachment zone 56 which extends in the longitudinal direction along the lapped edge 52 of the second panel 46 and along the remote end of the second flap 42. As can be seen from FIG. 2, the first and second attachment zones are on opposite sides of the first and second seams 30, 40.

Furthermore, it can be seen that the first flap 32 extends laterally away from a center of the first panel 44 towards a center of the second panel 46 and the second flap 42 extends laterally away from a center of the second panel 46 towards a center of the first panel 44.

The attachment of the first and second panels to the respective flaps may be by a variety of methods. In this embodiment, the attachment is by tacking or sewing. However, the attachment can also or alternatively be by gluing, bonding together with heat seal equipment, or other attachment method.

As has been explained above, attachment methods may result in perforations in the panels which may allow radiation to leak through or at least a risk of splitting of the core material. In this embodiment, the first panel laps the second panel across the second attachment zone to provide a continuous protective covering of the second attachment zone, and the second panel laps the first panel across the first attachment zone to provide a continuous protective covering of the first attachment zone. As a result, any perforations or splitting of the panels in the attachment zones are shielded by a continuous region of the other panel, thereby inhibiting radiation leakage through the garment as a result of these perforations or splits.

FIG. 3 shows the cross section of the garment with the layers close together and stitched across to close the seam arrangement as they would be while the garment is being worn. In this embodiment, the first and second attachment zones extend the entire length of the region in which the first and second panels meet; however, this is not necessary in every embodiment.

In this embodiment, the first and second panels are lapping over the entire length of the region in which the first and second panels meet, which in this embodiment is the length of the first and second seams.

It is well documented that the breast is at great risk of developing radiation induced breast cancer cells. The embodiments described herein allow a garment to be fitted much more closely and cover more tissue than previously achieved conventionally. Therefore, these embodiments can provide radiation garments more suited to the female form to minimize the radiation exposure to the breast, as well as other sensitive organs such as the lymph nodes located in the axillary area.

A further advantage of embodiments described herein is that while the front panels of radiation protection garments are traditionally wrapped by approximately 20 cm to allow for generic fitting across the breast/chest area, embodiments described herein can remove that requirement, thus reducing the overall weight of the product by approximately 400 gms.

Although the embodiments described above have first and second flaps, this is not necessary in every embodiment. In some embodiments, the panels can be attached directly to the main bodies of the first and fourth sections respectively, or the main bodies of the second and third sections respectively.

Although the embodiments described above are particularly advantageous for female apron wearers, the seam and panel arrangement described herein can be used for providing any desired shape to many types of personal radiation protection garment and can be used for male or female wearers.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

I claim:

1. A personal X-ray radiation protection garment, including:
    a first layer;
    a second layer;
    a protective layer between the first and second layers;
    wherein said first layer includes first and second sections joined at a first seam, and said second layer includes third and fourth sections joined at a second seam;
    wherein the said first and second seams are aligned;
    wherein said first and second seams are flat open seams;
    wherein said protective layer includes first and second partially lapping X-ray radiation-proof protective panels, said first panel being attached to said first layer at a first attachment zone and said second panel being attached to the second layer at a second attachment zone;
    wherein each of the first and second panels includes a substantially two-dimensional sheet; and wherein said first and second partially lapping X-ray radiation-proof protective panels are configured to slide against said first layer and said second layer, enabling lateral movement between said panels without separation of said panels; and wherein said first and second panels are equipped with lapped edges disposed on opposite sides of first and second seams so that, radially between the first and second seams, the first and second panels overlap;
    wherein said first panel laps said second panel across the second attachment zone to provide a continuous radiation-blocking protective covering of the second attachment zone, and said second panel laps said first panel across said first attachment zone to provide a continuous protective covering of said first attachment zone;

wherein the first and second attachment zones are on opposite sides of the first and second seams;

wherein said first layer, including said first and second sections, is arranged such that said first and said second sections are configured to move apart but not separate from one another;

wherein said first and second partially lapping X-ray radiation proof protective panels are equipped with a lead resin mix;

wherein said second layer, including said third and said fourth sections, is arranged such that said third and said fourth sections are configured to move apart but not separate from one another;

wherein between the said first and second seams, the said first and second panels lap;

wherein said panels meet in a region of seam arrangements;

wherein said seam arrangements extend in a curved configuration to form a convex 3D shape; and wherein the garment is a jacket-type garment configured to close via a zipper.

2. The garment of claim 1, wherein the said first attachment zone includes perforations in the said first panel and the said second attachment zone includes perforations in the second panel.

3. The garment of claim 1, wherein the first and second seams extend in a longitudinal direction, and wherein the first and second attachment zones substantially extend in the longitudinal direction.

4. The garment of claim 3, wherein the first attachment zone is at a substantially longitudinal edge of the first panel and the second attachment zone is at a substantially longitudinal edge of the second panel.

5. The garment of claim 4, wherein the first layer includes a first flap, and the second layer includes a second flap;

wherein said second flap extends from a second seam radially internally with respect to the garment towards said first layer; and wherein the first attachment zone is on the first flap and the second attachment zone is on the second flap.

6. The garment of claim 5, wherein the first and second flaps extend laterally away from each other.

7. The garment of claim 6, wherein each of the first and second flaps extends laterally away from the first and second seams.

8. The garment of claim 7, wherein the first attachment zone is at a remote end of the first flap and the second attachment zone is at a remote end of the second flap.

9. The garment of claim 7, wherein the first, second, third, and fourth sections are fabric sections.

10. The garment of claim 9, wherein the first panel laps a lapped edge of the second panel and the second panel laps a lapped edge of the first panel.

11. The garment of claim 10, wherein the first panel includes a bound edge opposite and adjacent to the lapped edge of the first panel wherein the first panel is secured to the first and second layer at the bound edge of the first panel to prevent the first panel from being pulled out of lapping relationship with the second panel.

12. The garment of claim 11, wherein the second panel includes a bound edge opposite and/or adjacent to the lapped edge of the second panel wherein the second panel is secured to the first and second layer at the bound edge of the second panel to prevent the second panel from being pulled out of lapping relationship with the first panel.

13. The garment of claim 12, wherein the first panel laps no more than 50% of the area of the second panel and the second panel laps no more than 50% of the area of the first panel.

14. The garment of claim 12, wherein the first panel laps no more than 25% of the area of the second panel and the second panel laps no more than 25% of the area of the first panel.

* * * * *